United States Patent
Norman et al.

(10) Patent No.: US 6,517,823 B1
(45) Date of Patent: Feb. 11, 2003

(54) HIGH GLOSS MASCARA

(75) Inventors: Greg Norman, Woodbridge, NJ (US); Mohamed Kanji, Edison, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/492,403

(22) Filed: Jan. 27, 2000

(51) Int. Cl.$^7$ .............. A61K 7/06; A61K 9/00; A61K 6/00
(52) U.S. Cl. .............. 424/70.7; 424/400; 424/401; 424/64; 424/70.1
(58) Field of Search ............... 424/400, 401, 424/64, 70.1, 70.7

(56) References Cited

U.S. PATENT DOCUMENTS

| | | | |
|---|---|---|---|
| 4,507,279 A | 3/1985 | Okuyama et al. | 424/63 |
| 5,534,247 A | * 7/1996 | Franjac et al. | 424/70.7 |
| 5,688,493 A | * 11/1997 | Sugawara et al. | 424/61 |
| 5,849,278 A | 12/1998 | Piot et al. | |
| 5,874,072 A | * 2/1999 | Alwattari et al. | 424/70.7 |
| 5,932,197 A | * 8/1999 | Arnaud | 424/64 |
| 5,961,998 A | 10/1999 | Arnaud et al. | 424/401 |
| 6,153,206 A | 11/2000 | Anton et al. | |
| 6,296,858 B1 | * 10/2001 | Agostini et al. | 424/401 |

FOREIGN PATENT DOCUMENTS

| | | |
|---|---|---|
| EP | 0 557 196 A1 | 8/1993 |
| EP | 0 847 753 A2 | 6/1998 |
| EP | 0795 322 | 10/1998 |
| EP | 0898 960 | 3/1999 |

OTHER PUBLICATIONS

Derwent Abstract of EP 0 847 753 A2, Jun. 17, 1998.
Derwent English Language Abstract of EP 0898 960, Mar. 3, 1999.
Derwent English Language Abstract of EP 0795 322, Oct. 28, 1998.

* cited by examiner

Primary Examiner—Thurman K. Page
Assistant Examiner—Rachel M. Bennett
(74) Attorney, Agent, or Firm—Finnegan, Henderson, Farabow, Garrett & Dunner, L.L.P.

(57) ABSTRACT

An embodiment of the present invention is a cosmetic composition with enhanced gloss properties. The cosmetic compositions of the present invention contain at least one film former with high gloss properties, i.e., a glossy film former having a gloss effect measurement of greater than 50%, at least one thickener, and at least one wax. The combination of the thickener and the wax are present in a combined amount such that the gloss effect measurement of the composition is greater than 50%. The glossy cosmetic composition may be a mascara, eyeliner, lip gloss, or blush.

41 Claims, No Drawings

HIGH GLOSS MASCARA

The present invention relates to a cosmetic composition, in particular a mascara composition, with enhanced gloss properties. The cosmetic compositions of the present invention contain at least one glossy film former, at least one thickener, and at least one wax and have a gloss effect measurement of greater than 50%.

Many conventional cosmetics, including non-pigmented and pigmented cosmetics such as mascara, eyeliner, lip gloss, and blush, have a matte appearance upon application and drying. The applied cosmetic quickly loses its fresh, glossy, or wet look and subsequently appears dull and dry regardless of the addition of pigments and other emollients. For example, conventional mascara formulations have a matte appearance upon application and drying on eye lashes. The wet or glossy look of freshly applied mascara quickly fades and as a result the eyes are left with a dull or dry appearance.

The lack of a glossy appearance is observed regardless of whether an emulsion-based formula or a solvent-based formula is used. This may be due, for example, to the combination of ingredients in a particular cosmetic composition formula or to the small surface area that a cosmetic composition generally covers. In emulsion-based cosmetics, the evaporation of solvents or water leaves behind a layer of waxes, pigments, film formers, and emulsifiers which give a matte look. In the case of solvent-based cosmetics, when the solvent evaporates, again a layer of waxes and pigments is left behind, giving a matte appearance.

Therefore, there remains a need to develop a glossy or wet look appearance for all cosmetic compositions, similar to the glossy/wet look for nail enamels currently on the market. Preferably, a glossy or wet look cosmetic composition would result in a fresh, healthy, and just-applied look, long after the cosmetic composition was applied and had dried.

To achieve these and other advantages, in whole or in part, the present invention is, in one embodiment, drawn to a composition comprising at least one glossy film former, at least one thickener, and at least one wax. The at least one glossy film former has a gloss effect measurement of greater than 50% and the at least one thickener and the at least one wax are present in a combined amount such that the gloss effect measurement of the composition is greater than 50%. The cosmetic compositions of the present invention include, but are not limited to, mascara, including hair mascara, eyeliner, lip gloss, and blush. Glossy film formers, thickeners, and waxes useful in the practice of the invention will be discussed in greater detail below.

In another embodiment, the present invention relates to a method of providing gloss to a cosmetic composition by including in the composition at least one glossy film former having a gloss effect measurement of greater than 50%, at least one thickener and at least one wax. The at least one thickener and the at least one wax are present in a combined amount such that the gloss effect measurement of the composition is greater than 50%.

The present invention is also drawn to a method of making a glossy cosmetic composition by selecting at least one glossy film former having a gloss effect measurement greater than 50% and adding to it at least one thickener and at least one wax in a combined amount such that the gloss effect measurement of the composition is greater than 50%.

Reference will now be made in detail to embodiments of the invention.

Advantageously, the present invention results in a cosmetic composition with high gloss properties. In one embodiment, the present invention relates to a cosmetic composition comprising at least one glossy film former having a gloss effect measurement of greater than 50%, at least one thickener, and at least one wax. The at least one thickener and the at least one wax are present in a combined amount such that the gloss effect measurement of the composition is greater than 50%. The cosmetic compositions may be chosen from, but are not limited to, mascara, including hair mascara, eyeliner, lip gloss, and blush. In a preferred embodiment, the cosmetic compositions are emulsified water and oil compositions. In another embodiment, the cosmetic compositions may be organic solvent based depending on the glossy film former, the thickener, and the wax chosen.

In the context of the present invention, a glossy film former is defined as a film former with a gloss reading of "semigloss" or higher as measured by a gloss meter. A gloss meter, which is commonly used in the nail polish art, measures the amount of light reflected from the surface or film of interest, i.e., the "gloss effect." The gloss effect is quantified as a % reflectance, which can be categorized as dull (50% or less), semi-glossy (50%–60%), glossy (60%–70%), or very glossy (>70%). For example, a very glossy white ceramic tile has a gloss meter reading of 83.2% while the average gloss meter reading for nail polish is greater than 70% and preferably greater than 80% depending on the type of nail polish tested.

In a preferred embodiment, a cosmetic composition of the present invention has a gloss effect measurement of greater than 60%, more preferably greater than 70% and still more preferably greater than 80%. More details regarding specific types of glossy film formers are given below.

As mentioned above, the evaporation of solvents or water leaves behind a layer of waxes, pigments, film formers, and/or emulsifiers that give a matte appearance. Therefore, in order for a cosmetic composition to dry so that it still looks glossy or wet, each category of ingredients used in a particular composition needs to be evaluated in order to determine the effects of each on the level of gloss produced. For example, the present inventors evaluated the three following categories of ingredients: a) film formers; b) thickeners, and c) waxes. The inventors found that certain combinations of glossy film former, thickener, and wax produced a cosmetic composition that appeared glossy or wet-looking upon drying. To achieve this effect, the inventors used glossy film formers which have a gloss effect measurement of greater than 50% and the thickeners and waxes present in a combined amount such that the gloss effect measurement of the composition is greater than 50%.

Film formers/resins useful in the cosmetic composition of the invention are also able to provide the cosmetic composition with properties such as good adherence to substrates, flexibility, good wearability, good drying time, non-tackiness, good retention, transfer-resistance, and/or low migration over time, among other properties. Preferably, film formation occurs when the solvent evaporates at a rate that allows a film to form continuously and substantially free from imperfections.

The gloss properties of numerous film formers and mixtures of film formers are evaluated by applying a film former or mixture of film formers onto a substrate such as a ceramic tile. Once dry, the gloss properties of the film former(s) are measured with a gloss meter. In addition, the film former(s) can be visually evaluated for shine, water resistance, smudging, hardness and other properties. Based on these results, the skilled artisan will know how to choose a glossy film former having the desired gloss properties as well as other desirable film forming properties. In a preferred embodiment, the at least one film former would have the best observable gloss, water resistance, smudge resistance, hardness, transfer-resistance and other desirable properties.

Based on evaluations of gloss properties like those described above, it was found that glossy film formers useful in the present invention include, but are not limited to, copolyester, ethyl ester PVM/MA copolymer, VA/butyl maleate/isobornyl acrylate terpolymer, VA/acrylates copolymer, ethyl acrylates/methyl methacrylates copolymer, PVP, styrene/acrylates copolymer, VA/ethylene copolymer, methacrylate copolymer, dimethicone/sodium PG-propyldimethicone thiosulfate copolymer, polyvinyl alcohol, PVPNA copolymer, and PPG-17/urethane/DMPA copolymer.

In one embodiment, a glossy film former is chosen by applying a mixture of a film former and a pigment to a substrate and measuring the gloss of the mixture with a gloss meter. The pigment adds color to the mixture, making it easier to see the gloss of the applied mixture. A film former that has a gloss effect measurement of greater than 50% is chosen, with the level of gloss effect varying above 50% depending on how glossy an end product is desired.

Once the film former is selected, one must choose a thickener that provides the desired viscosity for the cosmetic composition. In particular, a desirable thickener should not substantially reduce the gloss properties of the at least one glossy film former and preferably is water soluble or water dispersible. To determine if a thickener affects the gloss of the film former, a glossy film former and a thickener may be combined and applied to a substrate. Upon drying, the gloss of the composition is measured. If the glossy film former has substantially retained its glossy characteristics, the thickener is suitable for use with the glossy film former to provide a glossy cosmetic composition.

Thickeners that do not substantially reduce the gloss properties of a glossy film former include organic thickeners and inorganic thickeners. Suitable organic thickeners include, but are not limited to, PEG-8 dioleate, available from Lipo as LIPOPEG® 4-DO, polyglyceryl-2 diisostearate, available from Alzo as DERMOL® DGDIS, nonionic associative polymers, such as PEG-150/decyl/SMDI copolymer and PEG-150/stearyl/SMDI copolymer, available from ISP as Aculyn 44® and Aculyn 46®, respectively, nonionic non-associative polymers, anionic associative polymers, such as acrylates/steareth-20 methacrylate copolymer, available from ISP as Aculyn 22®, and anionic non-associative polymers such as acrylates copolymer, available from ISP as Aculyn 33®. Suitable inorganic thickeners include, but are not limited to, Laponite® XLG (Na Mg silicate) and MSS 500/N (silica). In a preferred embodiment, the thickener is organic and is chosen from the Aculyn® family of polymers available from ISP. In a further preferred embodiment, the thickener is an anionic polymer. The thickener may also be a mixture of thickeners, such as a mixture of associative and nonassociative polymers.

Waxes useful in the present invention provide one or more of the following properties, including but not limited to, bulking, texture, and a degree of water resistance, and should also not substantially reduce the gloss properties of a glossy film former. The same experiment may be repeated as above, i.e., combining a wax with a glossy film former or adding a wax to a glossy film former and thickener mixture. If the glossy film former has substantially retained its glossy characteristics, the wax is suitable for use with the glossy film former and/or thickener chosen to provide a glossy cosmetic composition. Waxes that do not substantially reduce the gloss properties of a glossy film former include, but are not limited to, lanolin alcohol, bayberry (myrica cerifera) wax, PEG-200 hydrogenated castor oil dimer/IPDI, and behenamidopropyl-dimethylamine behenate.

In a preferred embodiment, the cosmetic composition of the present invention uses waxes that do not substantially reduce the gloss effect of the at least one glossy film former. However, some waxes which appear initially to dull certain glossy film formers may still be utilized in a formulation which produces a glossy effect. The skilled artisan, by adjusting the concentration of each of the at least one glossy film former, at least one thickener and at least one wax can routinely determine parameters which substantially maintain the gloss properties of a specific film former. Additionally, not all glossy film formers are compatible with each thickener and each wax.

One of skill in the art, using the procedures described herein, may routinely vary the specific film formers, thickeners and waxes used in order to determine which combinations and mixtures of the three ingredients result in the glossy cosmetic compositions envisaged. The skilled artisan will also vary the percentages of film former(s), thickener(s) and wax(es) in a glossy cosmetic composition to achieve the desired glossy effect. A person skilled in the art will also know how to formulate and prepare a composition which has the desired properties, taking into account the compatibility of other materials used in addition to the glossy film formers, thickeners, and waxes.

Depending on the application envisaged, the concentration of glossy film former in the inventive composition may vary considerably. One of skill in the art will be able to determine routinely the preferred concentration of glossy film former depending on the application and the properties desired. In one representative embodiment, the compositions of the present invention contain at least one glossy film former present in an amount of from 0.5% to 50% by weight relative to the weight of the total composition, at least one thickener present in an amount of from 0.05% to 15% by weight, and at least one wax present in an amount of from 1% to 20% by weight.

Other film formers may be utilized as glossy film formers or as additional film formers that do not significantly reduce the gloss properties of any glossy film formers present. The additional film formers useful in the practice of the invention may be chosen from, but are not limited to, PVP, acrylates, and urethanes; synthetic polycondensate polymers, synthetic free-radical polymers, or synthetic ionic polymers; polymers of natural origin such as wheat protein film formers and mixtures thereof; celluloses and modified celluloses such as hydroxyethylcellulose; di-block, tri-block or radial block copolymer film formers such as KRATON® film formers; vinylpyrrolidone/vinyl acetate (PVPNA) copolymers such as the Luviskol® VA grades (all ranges) from BASF Corporation and the PVPNA series from ISP; acrylic fluorinated emulsion film formers including Foraperle® film formers such as Foraperle® 303 D from Elf Atochem, although Foraperle® may not be preferable for some cosmetic formulations; GANEX® copolymers such as Butylated PVP, PVP/Hexadecene copolymer, PVP/Eicosene copolymer or tricontanyl; Poly (vinylpyrrolidone/diethylaminoethyl methacrylate) or PVP/Dimethyl-aminoethylmethacrylate copolymers such as Copolymer 845; Resin ACO-5014 (Imidized IB/MA copolymer); other PVP based polymers and copolymers; silicone gums; cyclomethicone and dimethicone crosspolymers; trimethyl siloxysilicates such as SR 1000, SS4230, or SS4267 available from GE Silicones; alkyl cycloalkylacrylate copolymers; Mexomere® film formers and other allyl stearate/vinyl acetate copolymers (allyl stearateNA copolymers); Polyolprepolymers such as PPG-12/SMDI copolymer and Poly(oxy-1,2-ethanediyl) α-hydro-ω-hydroxy-polymer with 1,1'-methylene-bis-(4-isocyanatocyclohexane) available from Barnet; Avalure® AC Polymers (Acrylates Copolymer) and Avalure® UR polymers (Polyurethane Dispersions), available from BFGoodrich; other film formers disclosed in the *International Cosmetic Dictionary and Handbook Vol.* 2 ($7^{th}$ ed. 1997), more particularly the film formers disclosed on pages 1636–1638, or any other film formers known within the practice of the cosmetic and pharmaceutical arts which one skilled in the art may determine to be compatible. The disclosure of the *International Cosmetic Dictionary and Handbook Vol.* 2, pages 1636–1638, is hereby incorporated by reference.

The glossy film former(s) or additional film former(s) may improve smoothness or spreadability, water-resistance, transfer resistance properties, flexibility, or other cosmetic or pharmaceutical properties desired by one of skill in the art.

The concentration of additional film formers may be determined by one of skill in the art and may vary considerably based on the application. Other compositions known in the art that are.capable of leaving a film on keratinous fibers may also be added to the compositions of the invention, including emollients and other ingredients usually employed in the field envisaged. These added ingredients may include gels, oils, waxes, preservatives, thickening agents, solvents, surfactants, emollients, humectants and other ingredients that do not substantially reduce the glossy properties of the compositions of the invention.

Emollients and/or humectants that may be used in the compositions of the invention include glycerin, propylene glycol, cyclomethicone, dimethicone, and emollients and other similar ingredients disclosed in the *International Cosmetic Dictionary and Handbook Vol.* 2 ($7^{th}$ ed. 1997), more particularly the emollients disclosed on pages 1656–1661. The disclosure of the *International Cosmetic Dictionary and Handbook Vol.* 2, pages 1656–1661, is hereby incorporated by reference.

The compositions of the invention may further include formulation aids which are usually employed in the field of application envisaged. The formulation aids used in the present invention can be, but are not limited to, fatty substances. Useful fatty substances include, but are not limited to, organic and organosilicone emulsifiers for water-in-oil systems. Examples of organic emulsifiers include any ethoxylated surfactants known in the art such as Polysorbate-20, Laureth-7, Laureth4, Sepigel® 305 available from SEPPIC and other similar ingredients disclosed in the *International Cosmetic Dictionary and Handbook Vol.* 2 ($7^{th}$ ed. 1997), more particularly the emulsifiers disclosed on pages 1679–1687. The disclosure of the *International Cosmetic Dictionary and Handbook Vol.* 2, pages 1679–1687, is hereby incorporated by reference. Examples of organosilicone emulsifiers include cetyl dimethicone copolyol-polyglyceryl-4-isostearate-hexylaurate (ABIL® WE 09) available from Goldschmidt Chemical Corporation, Cetyl Dimethicone Copolyol (ABIL® EM 90), (ABIL® EM 97), Laurylmethicone Copolyol (5200), Cyclomethicone (and) Dimethicone Copolyol (DC 5225 C and DC 3225 C) available from GE Silicones, Cyclopentasiloxane & Dimethicone Copolyol (GE SF 1528) or any other formulation aids known by one of skill in the art. Other fatty substances useful as formulation aids include but are not limited to, silicones in esterified or unesterified liquid form or in esterified solid form, such as behenate dimethicone; and non-silicone fatty substances including oils such as vegetable and mineral oil; animal and/or synthetic waxes such as beeswax, parafin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD.

These substances may be selected variously by the person skilled in the art in order to prepare a composition which has the desired properties, for example, consistency or texture.

Plasticizers may also be added to the compositions to improve the flexibility and cosmetic properties of the resulting formulation. Plasticizers are materials which soften synthetic polymers. They are frequently required to avoid brittleness and cracking of film formers. One skilled in the art may routinely vary the amount of plasticizer desired based on the properties desired and the application envisaged. Plasticizers useful in the practice of the invention include lecithin, polysorbates, dimethicone copolyol, glycols, citrate esters, glycerin, dimethicone, and other similar ingredients disclosed in the *International Cosmetic Dictionary and Handbook Vol.* 2 ($7^{th}$ ed. 1997), more particularly the plasticizers disclosed on page 1654. The disclosure of the *International Cosmetic Dictionary and Handbook Vol.* 2, page 1654, is hereby incorporated by reference.

Pigments may also be included in the compositions of the invention. A pigment should be understood to mean inorganic or organic, white or colored particles. Representative pigments that may be used in the practice of the invention, provided they do not substantially reduce the gloss properties of the glossy film former(s), include carbon black, titanium dioxide, D & C Red No. 7 Calcium Lake, D & C Red No. 21 Aluminum Lake, Iron Oxides, FD & C Yellow No. 5 Aluminum Lake, FD & C Blue no. 1 Aluminum Lake and any other pigment or treated pigment known in the cosmetic arts. The amount of pigment may vary depending on the application envisaged, however, it has been found that increased amounts of pigment may result in a matte effect.

The compositions of the present invention may also contain dispersion enhancing agents such as the polysaccharide resin KAMA®, available from KAMA International Corp., Duluth, Ga. Dispersion enhancing agents are especially preferred in pigmented products.

Fillers and mothers-of-pearl may also be added to the formulations to modify the texture of the composition and the matteness/gloss effect. Fillers should be understood to mean lamellar or non-lamellar, inorganic or synthetic, colorless or white particles. Mothers-of-pearl should be understood to mean irridescent particles produced especially by certain mollusks in their shell or else synthesized. Pearling agents that may be used in the practice of the invention include mica, iron oxides, titanium dioxide and any other pearling agent known in the cosmetic arts.

It is also possible to add to the composition of the invention any customary additive from the field of compositions to be applied in any cosmetic formulation including cosmetic mascara, eyeliner, lip gloss, and blush, such additives being chosen from preservatives, in particular water-soluble preservatives; antifoaming agents; wetting agents; chelators such as EDTA and salts thereof; UV-screening agents; perfumes; fillers; antioxidants; essential oils; cosmetic or pharmaceutical active agents; moisturizers; vitamins and derivatives thereof; biological materials and derivatives thereof.

The person skilled in the art will of course take care to choose the optional additional compounds and/or their quantity in such a way that the advantageous properties of the composition according to the invention are not, or are substantially not, impaired by the envisaged addition.

In addition to cosmetic compositions, the present invention relates to a method of providing gloss to a cosmetic composition by including in the composition at least one glossy film former having a gloss effect measurement of greater than 50%, at least one thickener, and at least one wax. The at least one thickener and the at least one wax are present in a combined amount such that the gloss effect measurement of the composition is greater than 50%. Gloss may be provided to numerous cosmetic compositions including, but not limited to, the ones described above.

Another embodiment of the present invention encompasses a method of making a glossy cosmetic composition by selecting at least one glossy film former having a gloss effect measurement greater than 50% and adding to it at least one thickener and at least one wax in a combined amount such that the gloss effect measurement of the composition is greater than 50%.

The invention will be further clarified by the following examples, which are intended to be illustrative of the invention, but not limiting thereof.

EXAMPLES

Example 1

Evaluation of Film Formers

The gloss properties of film formers were evaluated by preparing, for each film former tested, a solution comprising 1 part black iron oxide with 5 parts film former solids. The mixture was applied to a glass plate and allowed to dry overnight. The gloss properties of the resulting film were measured with a gloss meter (BYK Gardener, micro-PRI-gloss, Model 4525).

The gloss or shine measurement for each of 26 film formers is shown below. The film formers were also evaluated for their water resistance, smudging and hardness characteristics.

| | Film Former (CTFA Name) | Trade Name | Supplier | Shine | Water resistance | Smudging | Hardness |
|---|---|---|---|---|---|---|---|
| 1 | Polyvinyl Acetate | Vinac ® XX230 | Air Products | dull | slight | no | hard, brittle |
| 2 | PVP/Silicone | Polymer ACP-1204 | ISP | dull | slight | yes | crumbly |
| 3 | Copolyester | 1350 Copolyester | Eastman | semigloss | none | no | soft, pliable |
| 4 | Sodium Polystyrene Sulfonate | Flexan ® 130 | Nat'l Starch | dull | none | no | brittle |
| 5 | Ethyl Ester PVM/MA Copolymer | Omnirez ® 2000 | ISP | very glossy | yes | no | hard, brittle |
| 6 | VA/Butyl Maleate/ Isobornyl Acrylate | Advantage Plus | ISP | very glossy | yes | no | hard, brittle |
| 7 | VA/Acrylates Copolymer | Gelva ® TS-100 | Monsanto | semigloss | yes | no | soft, pliable |
| 8 | Acrylates Copolymer | Carboset ® XL-28 | B. F. Goodrich | dull | yes | no | hard, brittle |
| 9 | PVP/Polycarbamyl Polyglycol | Pecogel ® H-12 | Phoenix | dull | none | no | hard, brittle |
| 10 | Ethyl Acrylates/ Methyl Methacrylates | Daitosol ® | KOBO | very glossy | yes | no | soft, pliable |
| 11 | PVP | K-30 | ISP | semigloss | none | no | hard, brittle |
| 12 | PVP | K-60 | ISP | semigloss | none | no | hard, brittle |
| 13 | Styrene/Acrylates Copolymer | Joncryl ® 77 | Johnson Wax | glossy | yes | no | brittle |
| 14 | VA/Ethylene Copolymer | Airflex ® 809 | Air Products | glossy | yes | no | soft, pliable |
| 15 | Methacrylate Copolymer | Copolymer 958 | ISP | very glossy | none | no | brittle |
| 16 | PVP/Dimethylamino ethylmethacrylates Copolymer | Copolymer 845 | ISP | dull | none | no | brittle |
| 17 | Dimethicone/Sodium PG-Propyl- dimethicone ThiosulfateCopolymer | Abil ® S201 | GoldSchmidt | very glossy | yes | no | very soft |
| 18 | Polyvinyl alcohol | Airvol ® 205 | Air Products | glossy | none | no | semi-soft |
| 19 | VCAP/VP/ Imidazolium sulfate | Luviquathold ® | BASF | dull | none | — | — |
| 20 | PVP/VA Copolymer | Luviskol ® VA37E | BASF | very glossy | slight | no | brittle |
| 21 | PVP/VA Copolymer | Luviskol ® VA73W | BASF | very glossy | none | no | brittle |
| 22 | PVP/VA Copolymer | Luviskol ® VA55E | BASF | very glossy | slight | no | hard, brittle |
| 23 | PVP/VA Copolymer | PVP/VA S-630 | ISP | glossy | none | no | hard, brittle |

-continued

| Film Former (CTFA Name) | Trade Name | Supplier | Shine | Water resistance | Smudging | Hardness |
|---|---|---|---|---|---|---|
| 24 PVP/VA Copolymer | PVP/VA E-735 | ISP | very glossy | none | no | hard, brittle |
| 25 PPG-17/Urethane/ DMPA Copolymer | Avalure ® UR-450 | B. F. Goodrich | glossy | yes | no | soft, pliable |
| 26 Polyquaternium-11 | Polyquat 11SL | Inter'l Sourc. | dull | yes | no | hard, brittle |

Example 2

Evaluation of Thickeners

The effect of eight different thickeners on the gloss properties of a glossy film former was evaluated by preparing the following base mixture:

80.9% $H_2O$;

13.5% of the glossy film former PVP-K30; and 5.6% of the pigment iron oxide.

A thickener at the weight % listed below was then added to the base mixture and the resulting mixture was homogenized.

1) 3% Aculyn 33®+97% base mixture
2) 2% Laponite® XLG+98% base mixture
3) 13% MSS 500/N+87% base mixture
4) 4.85% Aculyn 22®+95.15% base mixture
4a) 2.00% Aculyn 22®+98% base mixture
5) 2.00% Cellulose Gum+98% base mixture
6) 2.00% Mg Al Silicate+98% base mixture
7) 1.00% Sepigel® 305+99% base mixture
8) 1.00% Keltrol® F+99% base mixture The thickener/glossy film former mixture was subsequently applied to a glass plate and allowed to dry overnight. The gloss properties of the resulting film were measured with a gloss meter (BYK Gardener, micro-PRI-gloss, Model 4525). The gloss or shine measurement for 8 thickener/glossy film former mixtures are shown below. There was no difference in shine between compositions 4 and 4a. The thickeners are listed from those that had the least effect on the gloss properties of the glossy film former (highest gloss retained) to those with the strongest dulling effect.

| | Thickener (CTFA Name) | Trade Name | Supplier | Gloss |
|---|---|---|---|---|
| 1 | Acrylates Copolymer | Aculyn 33 ® | ISP | Highest Gloss retained |
| 2 | Na Mg Silicate | Laponite ® XLG | Southern Clay | |
| 3 | Silica | MSS 500/N | KOBO | |
| 4 | Acrylates/Steareth-20 Methacrylates Copolymer | Aculyn 22 ® | ISP | |
| 5 | Cellulose Gum | Cellulose Gum | Aqualon | |
| 6 | Mg Al Silicate | Veegum ® HV | Vanderbilt | |
| 7 | Polyacrylamide (&) C13–14 Isoparaffin (&) Laureth-7 | Sepigel ® 305 | Seppic | |
| 8 | Xanthan Gum | Keltrol ® F | Calgon | dullest |

While not all thickener/glossy film former mixtures resulted in the same gloss reading, the addition of thickeners 1, 2, 3, or 4 did not result in a substantial reduction in the gloss properties of the glossy film former PVP-K30. Furthermore, the other thickeners tested may still be utilized in a composition of the present invention at different concentrations or when combined with other glossy film formers.

Example 3

Evaluation of Waxes

The gloss properties of waxes were evaluated by preparing the following base mixture:

| | |
|---|---|
| Water | 3.6% |
| Joncryl ® 77 (Glossy Film Former) | 4.6% |
| TEA | 1.5% |
| Stearic Acid | 3.0% |
| Iron Oxide (Pigment) | 6.0% |
| Wax being studied | 10% |

The mixture was subsequently applied to a glass plate and allowed to dry overnight. The gloss properties of the resulting film were measured with a gloss meter (BYK Gardener, micro-PRI-gloss, Model 4525). The gloss or shine measurement for each mixture containing one of the 11 different waxes in the table below was determined.

| | Wax (CTFA Name) | Trade Name | Supplier |
|---|---|---|---|
| 1 | Candelilla Wax | SP 75 | Strahl & Pitsch |
| 2 | PVP/Eicosene | Ganex ® v-220 | ISP |
| 3 | Lanolin Alcohol | Super Hartolan | Croda |
| 4 | Hydrogenated Fish Oil (&) Myricyl Alcohol (&) Cerotic Acid (&) Paraffin (&) Mellicid Acid | Bayberry Wax | Ross |
| 5 | Beeswax | SP453 | Strahl & Pitsch |
| 6 | Cerisin Wax | SP254 | Strahl & Pitsch |
| 7 | C20–40 alcohol | Performalcol 350 Alcohol | New Phase Tech. |
| 8 | PEG-200 Hydrogenated Castor Oil Dimer/IPDI | Polyderm ® PPI-CO-200 | Alzo |
| 9 | | AMS-C30 | D.C. |
| 10 | Behenamidopropyldi-methylamine Behenate | CATAMOL ® 220B | Phoenix Chemical |
| 11 | Paraffin Wax | | |

While Catamol® 220B (#10) had the least reduction in gloss properties of the glossy film former Joncryl® 77, followed by Polyderm® PPI-CO-200 (#8), and Bayberry Wax Sub. 1641 (#4), none of these three waxes substantially reduced the gloss properties of the glossy film former. The remaining waxes rendered the glossy film former fairly dull.

However, all of the waxes tested may still be utilized in a composition of the present invention at different concentrations than those tested or when combined with other glossy film formers. For example, Lanolin Alcohol was used as the wax in several of the mascara formulations described below and was found not to substantially reduce the gloss properties of the glossy film formers utilized.

Example 4

Glossy Mascara Formulations

A glossy film former or a mixture of glossy film formers, thickeners, and waxes were chosen using the methods described above. The ingredients were then used to formulate the glossy mascara formulations described below.

stirred until cooled to 60° C. at which point E was added. The resulting mixture was cooled to 30–35° C. while stirring.

The resulting mascara composition was measured for gloss using a gloss meter (BYK Gardener, micro-PRI-gloss, Model 4525). Glossy Mascara A had a gloss meter reading of 80% and therefore passed the gloss standards for a nail polish. As a comparative test, gloss measurements were taken for Great Lash® Mascara by Maybelline. The average gloss reading for Great Lash® Mascara was 3.15%. Thus,

Glossy Mascara A

| | Trade Name | CTFA Name | % | Supplier |
|---|---|---|---|---|
| A | Water | Water | 38.8 | |
| | Luviskol ® VA 73W | PVP/VA Copolymer | 20 | BASF |
| | Monoderm ®-18-100 | PEG-100 Stearyl Ether Dimer/PDI | 8 | Alzo |
| | Methylparaben | Methylparaben | 0.2 | |
| | Butylene Glycol | Butylene Glycol | 2 | |
| | Lipopeg ® 4-DO | PEG-8 Dioleate | 0.2 | Lipo |
| | Aculyn 22 ® | Acrylates/Steareth-20 Methacrylates Copolymer | 1.5 | ISP |
| | Aculyn 44 ® | C-10 Polycarbamyl Polyglycol Ester | 0.3 | ISP |
| B | Super Hartolan | Lanolin Alcohol | 3 | |
| | Black NF | Iron Oxide | 2 | Kobo |
| | Propylparaben | Propylparaben | 0.05 | |
| | Dermol ® DGDIS | Polyglyceryl-2 Diisostearate | 1 | Alzo |
| C | Water | Water | 5 | |
| | TEA | Triethanolamine | 0.55 | |
| | Joncryl ® 77 | Styrene/Acrylates Copolymer | 16 | |
| D | Sentry Simethicone | Simethicone | 0.1 | |
| E | Germall ® 115 | Imidazolidinylurea | 0.3 | |
| | Water | Water | 1 | |
| | | | 100 | |

Procedure: Ingredients in A were mixed together, stirred and heated to about 80–85° C. In a separate container ingredients in B were mixed, stirred and heated to about 80–85° C. A and B were blended together and homogenized for 10 minutes with a Silverson High Shear Homogenizer. Ingredients C were added to the homogenized mixture at 70° C. and the resulting mixture was homogenized for 10 more minutes. Ingredients D were added and the solution was the glossy mascaras of the present invention demonstrate a significant improvement in gloss properties over current mascaras.

It should be noted that a gloss meter works best when measuring a perfectly flat film. Due to the thick viscosity of mascara it is impossible to achieve a perfectly flat film, therefore, the uneven surface of the mascara lowers the gloss meter reading.

Glossy Mascara B

| | Trade Name | CTFA Name | % | Supplier |
|---|---|---|---|---|
| A | Water | Water | 36.8 | |
| | Luviskol ® VA 73W | PVP/VA Copolymer | 20 | BASF |
| | Monoderm ®-18-100 | PEG-100 Stearyl Ether Dimer/IPDI | 8 | Alzo |
| | Methylparaben | Methylparaben | 0.2 | |
| | Butylene Glycol | Butylene Glycol | 2 | |
| | Lipopeg ® 4-DO | PEG-8 Dioleate | 0.2 | Lipo |
| | Aculyn 22 ® | Acrylates/Steareth-20 Methacrylates Copolymer | 1.5 | ISP |
| | Aculyn 44 ® | C-10 Polycarbamyl Polyglycol Ester | 0.3 | ISP |
| B | Super Hartolan | Lanolin Alcohol | 3 | |
| | Black | Iron Oxide | 4 | |
| | Propylparaben | Propylparaben | 0.05 | |
| | Dermol ® DGDIS | Polyglyceryl-2 Diisostearate | 1 | Alzo |
| C | Water | Water | 5 | |
| | TEA | Triethanolamine | 0.55 | |
| | Joncryl ® 77 | Stynene/Acrylates Copolymer | 16 | |
| D | Sentry Simethicone | Simethicone | 0.1 | |

-continued

Glossy Mascara B

| | Trade Name | CTFA Name | % | Supplier |
|---|---|---|---|---|
| E | Germall ® 115 | Imidazalidinylurea | 0.3 | |
| | Water | Water | 1 | |
| | | | 100 | |

Procedure: Ingredients in A were mixed together, stirred and heated to about 80–85° C. In a separate container ingredients in B were mixed, stirred and heated to about 80–85° C. A and B were blended together and homogenized for 10 minutes with a Silverson High Shear Homogenizer. Ingredients C were added to the homogenized mixture at 70° C. and the resulting mixture was homogenized for 10 more minutes. Ingredients D were added and the solution was stirred until cooled to 60° C. at which point E was added. The resulting mixture was cooled to 30–35° C. while stirring.

Glossy Mascara C

| | Trade Name | CTFA Name | % | Supplier |
|---|---|---|---|---|
| A | Water | Water | 42.05 | |
| | Luviskol ® VA 73W | PVP/VA Copolymer | 18 | BASF |
| | Butylene Glycol | Butylene Glycol | 0.5 | |
| | Methylparaben | Methylparaben | 0.2 | |
| | Aculyn 22 ® | Acrylates/Steareth-20 methacrylates Copolymer | 3.2 | ISP |
| | Aculyn 33 ® | Acrylates | 1 | ISP |
| B | Super hartolan | Lanolin Alcohol | 3 | |
| | Propylparaben | Propylparaben | 0.05 | |
| | Iron Oxide | Iron Oxide | 0.5 | |
| | Dermol ® DGDIS | Polyglyceryl-2 Diisostearate | 1.5 | |
| | Lipopeg ® 4-DO | PEG-8 Dioleate | 0.3 | |
| C | Water | Water | 5 | |
| | TEA | Triethanolamine | 1.3 | |
| | Joncryl ® 77 | Styrene/Acrylates Copolymer | 22 | |
| D | Sentry Simethicone | Simethicone | 0.1 | |
| E | Germall ® 115 | Imidazolidinylurea | 0.3 | |
| | Water | Water | 1 | |
| | | | 100 | |

Procedure: Ingredients in A were mixed together, stirred and heated to about 80–85° C. In a separate container ingredients in B were mixed, stirred and heated to about 80–85° C. A and B were blended together and homogenized for 10 minutes with a Silverson High Shear Homogenizer. Ingredients C were added to the homogenized mixture and the resulting mixture was homogenized for 5 more minutes. Ingredients D were added and the solution was stirred until cooled to 60° C. at which point E was added. The resulting mixture was cooled to 30–35° C. while stirring.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the following claims and their equivalents.

We claim:
1. A cosmetic composition comprising:
   at least one glossy film former having a gloss effect measurement of greater than 50%,
   at least one thickener, and
   at least one wax,
   wherein said at least one thickener and said at least one wax are present in a combined amount such that the gloss effect measurement of said composition is greater than 50%.

2. A cosmetic composition according to claim 1, wherein said cosmetic composition is a mascara, eyeliner, lip gloss, or blush.

3. A cosmetic composition according to claim 1, wherein said at least one glossy film former is chosen from copolyester, ethyl ester PVM/MA copolymer, VA/butyl maleate/isobornyl acrylate, VA/acrylates copolymer, ethyl acrylates/methyl methacrylates, PVP, styrene/acrylates, VA/ethylene copolymer, methacrylate copolymer, dimethicone/sodium PG-propyldimethicone thiosulfate copolymer, Polyvinyl alcohol, PVPVA copolymer, and PPG-17/urethane/DMPA copolymer.

4. A cosmetic composition according to claim 1, wherein said at least one thickener is chosen from organic thickeners and inorganic thickeners.

5. A cosmetic composition according to claim 4, wherein said organic thickeners are chosen from PEG-8 dioleate, polyglceryl-2 diisostearate, nonionic associative polymers, nonionic non-associative polymers, anionic associative polymers, and anionic non-associative polymers.

6. A cosmetic composition according to claim 5, wherein said nonionic associative polymers are chosen from PEG-150/decyl/SMDI copolymer and PEG-150/stearyl/SMDI copolymer.

7. A cosmetic composition according to claim 5, wherein sa anionic associative polymers are chosen from acrylates/steareth-20 methacrylate copolymer and said anionic non-associative polymers are chosen from acrylates copolymer.

8. A cosmetic composition according to claim 4, wherein said inorganic thickeners are chosen from Na Mg silicate and silica.

9. A cosmetic composition according to claim 1, wherein said at least one wax is chosen from lanolin alcohol, bayberry wax, PEG-200 hydrogenated castor oil dimer/IPDI, and behenamidopropyl-dimethylamine behenate.

10. A cosmetic composition according to claim 1, further comprising at least one pigment.

11. A cosmetic composition according to claim 10, wherein said at least one pigment is chosen from carbon black and iron oxide.

12. A cosmetic composition according to claim 1, wherein said at least one glossy film former is present in a concentration ranging from 0.1% to 50%, relative to the weight of the total composition.

13. A cosmetic composition according to claim 1, wherein said at least one thickener is present in a concentration ranging from 0.1% to 20%, relative to the weight of the total composition.

14. A cosmetic composition according to claim 1, wherein said at least one wax is present in a concentration ranging from 1% to 10%, relative to the weight of the total composition.

15. A cosmetic composition according to claim 1, wherein said cosmetic composition has a gloss effect measurement of greater than 60%.

16. A cosmetic composition according to claim 1, wherein said cosmetic composition has a gloss effect measurement of greater than 70%.

17. A cosmetic composition according to claim 1, wherein said cosmetic composition has a gloss effect measurement of greater than 80%.

18. A method of providing gloss to a cosmetic composition comprising including in said composition:
   at least one glossy film former having a gloss effect measurement of greater than 50%,
   at least one thickener, and
   at least one wax,
   wherein said at least one thickener and said at least one wax are present in a combined amount such that the gloss effect measurement of said composition is greater than 50%.

19. A method of providing gloss to a cosmetic composition according to claim 18, wherein said cosmetic composition is a mascara, eyeliner, lip gloss, or blush.

20. A method of providing gloss to a cosmetic composition according to claim 18, wherein said at least one glossy film former is chosen from copolyester, ethyl ester PVM/MA copolymer, VA/butyl maleate/isobornyl acrylate, VA/acrylates copolymer, ethyl acrylates/methyl methacrylates, PVP, styrene/acrylates, VA/ethylene copolymer, methacrylate copolymer, dimethicone/sodium PG-propyldimethicone thiosulfate copolymer, Polyvinyl alcohol, PVPVA copolymer, and PPG-17/urethane/DMPA copolymer.

21. A method of providing gloss to a cosmetic composition according to claim 18, wherein said at least one thickener is chosen from organic thickeners and inorganic thickeners.

22. A method of providing gloss to a cosmetic composition according to claim 21, wherein said organic thickeners are chosen from PEG-8 dioleate, polyglceryl-2 diisostearate, nonionic associative polymers, nonionic non-associative polymers, anionic associative polymers, and anionic non-associative polymers.

23. A method of providing gloss to a cosmetic composition according to claim 22, wherein said nonionic associative polymers are chosen from PEG-150/decyl/SMDI copolymer and PEG-150/stearyl/SMDI copolymer.

24. A method of providing gloss to a cosmetic composition according to claim 22, wherein said anionic associative polymers are chosen from acrylates/steareth-20 methacrylate copolymers and said anionic nonassociative polymers are chosen from acrylates copolymers.

25. A method of providing gloss to a cosmetic composition according to claim 21, wherein said inorganic thickeners are chosen from Na Mg silicate and silica.

26. A method of providing gloss to a cosmetic composition according to claim 18, wherein said at least one wax is chosen from lanolin alcohol, bayberry wax, PEG-200 hydrogenated castor oil dimer/IPDI, and behenamidopropyl-dimethylamine beheate.

27. A method of providing gloss to a cosmetic composition according to claim 18, wherein said method results in a cosmetic composition having a gloss effect measurement of greater than 60%.

28. A method of providing gloss to a cosmetic composition according to claim 18, wherein said method results in a cosmetic composition having a gloss effect measurement of greater than 70%.

29. A method of providing gloss to a cosmetic composition according to claim 18, wherein said method results in a cosmetic composition having a gloss effect measurement of greater than 80%.

30. A method of making a glossy cosmetic composition comprising:
   selecting at least one glossy film former having a gloss effect measurement of greater than 50%; and
   adding to said at least one glossy film former at least one thickener and at least one wax in a combined amount such that the gloss effect measurement of said composition is greater than 50%.

31. A method of making a glossy cosmetic composition according to claim 30, wherein said glossy cosmetic composition is a mascara, eyeliner, lip gloss, or blush.

32. A method of making a glossy cosmetic composition according to claim 30, wherein said a t least one glossy film former is chosen from copolyester, ethyl ester PVM/MA copolymer, VA/butyl maleate/isobornyl acrylate, VA/acrylates copolymer, ethyl acrylate s/methyl methacrylates, PVP, styrene/acrylates, VA/ethylene copolymer, methacrylate copolymer, dimethicone/sodium PG-propyldimethicone thiosulfate copolymer, polyvinyl alcohol, PVP/VA copolymer, and PPG-17/urethane/DMPA copolymers.

33. A method of making a glossy cosmetic composition according to claim 30, wherein said at least one thickener is chosen from organic thickeners and inorganic thickeners.

34. A method of making a glossy cosmetic composition according to claim 33, wherein said organic thickeners are chosen from PEG-8 dioleate, polyglceryl-2 diisostearate, nonionic associative polymers, nonionic non-associative polymers, anionic associative polymers, and anionic non-associative polymers.

35. A method of making a glossy cosmetic composition according to claim 34, wherein said nonionic associative polymers are chosen from PEG-150/decyl/SMDI copolymer and PEG-150/stearyl/SMDI copolymer.

36. A method of making a glossy cosmetic composition according to claim 34, wherein said anionic associative polymers are chosen from acrylates/steareth-20 methacrylate copolymer and said anionic nonassociative polymers are chosen from acrylates copolymer.

37. A method of providing gloss to a cosmetic composition according to claim 33, wherein said inorganic thickeners are chosen from Na Mg silicate and silica.

38. A method of making a glossy cosmetic composition according to claim 30, wherein said at least one wax is chosen from lanolin alcohol, bayberry (myrica cerifera) wax, PEG-200 hydrogenated castor oil dimer/IPDI, and behenamidopropyl-dimethylamine beheate.

39. A method of making a glossy cosmetic composition according to claim 30, wherein said glossy cosmetic composition has a gloss effect measurement of greater than 60%.

40. A method of making a glossy cosmetic composition according to claim 30, wherein said glossy cosmetic composition having a gloss effect measurement of greater than 70%.

41. A method of making a glossy cosmetic composition according to claim 30, wherein said glossy cosmetic composition having a gloss effect measurement of greater than 80%.

* * * * *

UNITED STATES PATENT AND TRADEMARK OFFICE
CERTIFICATE OF CORRECTION

PATENT NO.   : 6,517,823 B1
DATED        : February 11, 2003
INVENTOR(S)  : Greg Norman et al.

It is certified that error appears in the above-identified patent and that said Letters Patent is hereby corrected as shown below:

<u>Column 14,</u>
Line 32, "PVPVA copolymer," should read -- PVP/VA copolymer, --.
Line 39, "polyglceryl-2" should read -- polyglyceryl-2 --.
Line 46, "sa anionic" should read -- said anionic --.

<u>Column 15,</u>
Line 35, "PVPVA copolymer," should read -- PVP/VA copolymer, --.
Line 43, "polyglceryl-2" should read -- polyglyceryl-2 --.

<u>Column 16,</u>
Line 20, "a t least one" should read -- at least one --.
Line 23, "acrylate s/methyl" should read -- acrylates/methyl --.
Line 28, "copolymers." should read -- copolymer. --.
Line 34, "polyglceryl-2" should read -- polyglyceryl-2 --.

Signed and Sealed this

Twenty-ninth Day of July, 2003

JAMES E. ROGAN
*Director of the United States Patent and Trademark Office*